United States Patent
Renn et al.

(10) Patent No.: US 7,408,057 B2
(45) Date of Patent: Aug. 5, 2008

(54) CLARIFIED HYDROCOLLOIDS OF UNDIMINISHED PROPERTIES AND METHOD OF PRODUCING SAME

(75) Inventors: Donald Walter Renn, Glen Cove, ME (US); Nancy Amelia Blake, Point Roberts, WA (US)

(73) Assignee: Marine Bioproducts Intenational, British Columbia (CA)

( * ) Notice: Subject to any disclaimer, the term of this patent is extended or adjusted under 35 U.S.C. 154(b) by 509 days.

(21) Appl. No.: 10/998,000

(22) Filed: Nov. 29, 2004

(65) Prior Publication Data
US 2005/0070704 A1    Mar. 31, 2005

Related U.S. Application Data

(63) Continuation-in-part of application No. 10/465,619, filed on Jun. 20, 2003, now abandoned, which is a continuation of application No. 09/609,870, filed on Jul. 3, 2000, now Pat. No. 6,586,590.

(51) Int. Cl.
    *C07H 1/06* (2006.01)
    *C08J 3/00* (2006.01)
    *C08J 3/16* (2006.01)

(52) U.S. Cl. .................. 536/128; 536/124; 536/114; 516/107

(58) Field of Classification Search ............ 516/77, 516/107; 536/4.1, 114, 124, 128
See application file for complete search history.

(56) References Cited

U.S. PATENT DOCUMENTS

| | | | |
|---|---|---|---|
| 3,346,556 A | 10/1967 | Foster | 536/52 |
| 3,928,322 A | 12/1975 | Suglyama et al. | |
| 3,973,008 A | 8/1976 | Sugiyama et al. | |
| 4,011,393 A * | 3/1977 | Trapasso | 536/114 |
| 4,320,226 A | 3/1982 | Tiefenthaler et al. | |
| 4,416,990 A | 11/1983 | Rinaudo et al. | |
| 4,582,714 A | 4/1986 | Ford et al. | |
| 4,735,935 A | 4/1988 | McAnalley | |
| 4,754,027 A | 6/1988 | Applegren | 536/114 |

(Continued)

FOREIGN PATENT DOCUMENTS

EP    0 549 230 A2    6/1993

(Continued)

OTHER PUBLICATIONS

Derwent Abstracts, week 198320, London: Derwent Publications Ltd., AN 88-164096/24, JP 63-101402 A (Mitsubishi Acetate Co., Ltd.), abstract.

(Continued)

*Primary Examiner*—Daniel S Metzmaier
(74) *Attorney, Agent, or Firm*—Paul A. Guss

(57) ABSTRACT

This invention relates to novel clarified hydrocolloids which substantially retain the physical properties of unclarified hydrocolloids. The invention also pertains to a novel process for making the clarified hydrocolloids. A process of producing a hydrocolloid which, when hydrated, forms a clear sol comprising: (a) soaking a hydrocolloid containing material dispersed in water until the hydrocolloid is hydrated; (b) stirring the hydrated hydrocolloid until a homogenous particulate containing sol is obtained; (c) removing insoluble particulates to produce a clarified sol; (d) removing remaining particulates in the clarified sol by filtration; and (e) recovering the clarified hydrocolloid from the filtrate.

2 Claims, 2 Drawing Sheets

U.S. PATENT DOCUMENTS

| | | | |
|---|---|---|---|
| 4,917,890 A | 4/1990 | McAnalley | |
| 5,116,631 A | 5/1992 | Sakamoto et al. | |
| 5,230,832 A | 7/1993 | Perlman | 516/107 |
| 5,756,720 A * | 5/1998 | Chowdhary | 536/124 |
| 5,800,818 A | 9/1998 | Prugnaud et al. | 424/744 |
| 5,962,053 A | 10/1999 | Merritt, II | |

FOREIGN PATENT DOCUMENTS

| | | |
|---|---|---|
| JP | 58-213001 | 12/1983 |
| JP | 59-17950 | 1/1984 |
| JP | 59-164301 | 9/1984 |
| JP | 61-166378 | 7/1986 |
| JP | 62-96061 | 5/1987 |
| JP | 62-126950 | 6/1987 |
| JP | 62-259550 | 11/1987 |
| JP | 63-35606 | 2/1988 |
| JP | 63-101402 | 5/1988 |
| JP | 63-105004 | 5/1988 |
| JP | 1-256366 | 10/1989 |
| JP | 3-43041 | 2/1991 |
| JP | 4-8257 | 1/1992 |
| JP | 4-11853 | 1/1992 |
| JP | 4-248460 | 9/1992 |
| JP | 5-55 | 1/1993 |
| JP | 5-199853 | 8/1993 |
| JP | 5-239105 | 9/1993 |
| JP | 5-239106 | 9/1993 |
| JP | 5-246860 | 9/1993 |
| JP | 6-345653 | 12/1994 |
| WO | 93/03047 | 2/1993 |
| WO | 94/00512 | 1/1994 |
| WO | 99/53968 | 10/1999 |

OTHER PUBLICATIONS

Patent Abstracts of Japan, Japan Patent Office, JP 63-035606A, Feb. 16, 1988.

* cited by examiner

CLARIFIED HYDROCOLLOIDS OF UNDIMINISHED PROPERTIES AND METHOD OF PRODUCING SAME

REFERENCE TO RELATED APPLICATION

This application is a continuation-in-part of application Ser. No. 10/465,619, filed Jun. 20, 2003, now abandoned, which is a continuation of application Ser. No. 09/609,870, filed Jul. 3, 2000, now U.S. Pat. No. 6,586,590 B1.

FIELD OF THE INVENTION

This invention relates to novel clarified hydrocolloids which substantially retain the physical properties of unclarified colloids. The invention also pertains to a novel process for making the clarified hydrocolloids.

BACKGROUND OF INVENTION

Hydrocolloids made from naturally occurring gums are used extensively in the food, pharmaceutical and cosmetics industries. Sols of most such hydrocolloids are opaque or translucent. When such hydrocolloids are clarified, the cost is usually uneconomical or there is inevitably a loss in the physical properties of the hydrocolloids compared to the unclarified colloids. This can, for example, include substantial loss in viscosity. Examples of naturally occurring gums used in making hydrocolloid sols are konjac, guar, locust bean and xanthan.

Konjac Glucomannan:

Konjac glucomannan, the first word sometimes spelled "konjak", is an acetylated glucomannan obtained from the tubers of the tropical plant, *Amorphophallus konjac*, commonly called "Devil's Tongue" because of its high content of oxalic acid. The konjac tuber is harvested following two or three year's growth, after which it has a diameter of 4-6". Processing steps include slicing, placing the slices on racks, sun or open fire drying, pulverization, dry or wet milling to remove the oxalic acid and some of the starch content which adheres to the konjac sacs, followed by sifting or air classification. These oval sacs are about 2 mm long and are composed mostly of konjac glucomannan encased in a proteinaceous membrane. Starch granules adhere to the membrane and much of these can be removed by a 30% alcohol (aq) wash. Native konjac glucomannan has a wide variation of acetyl content since it is both a storage and a structural polysaccharide. The more acetylated forms of the konjac glucomannan are water-soluble and the more deacetylated forms are water-insoluble. This is a simplistic statement, however, since a whole spectrum exists with respect to degree of acetylation with some of the soluble species on the edge of insolubility and minor changes in environment, such as salt concentration, excessive heating, removal of protective hydrocolloids or other molecules, etc., can lead to insolubilization.

Crude konjac flour, the most common commercial form, is a well-known foodstuff in China and Japan and has recently gained FDA approval in the U.S. as a fat replacer in meat. This application is based on the fact that when konjac glucomannan is heated with alkali, about pH=~7.5-11, deacetylation occurs and the resulting gel product is water insoluble and thermostable. The deacetylated gel or paste, commonly called "konnyaku" can even be fried at temperatures around 400° F. without melting or decomposing. If the gel formed by deacetylation is frozen and thawed, a tough, coherent spongeous mass is formed. Deacetylated konjac-containing films, foams, beads, and other forms can be prepared.

Konjac reacts with borate ion at alkaline pH to form amorphous gels as well as reacting synergistically with xanthan to form elastic gels.

As expected, there are numerous impurities in the crude, unclarified konjac. These include insoluble starches, cellulose, and nitrogen-containing impurities including proteins, many of which are derived from the konjac sac membrane. While crude konjac flours have numerous applications, as foods, as a soluble fiber source, as a fat replacement in meats, etc., the clarified form is preferable and in some applications, essential, for such applications as clear dessert gels, as a viscosifier or thickening agent for clear fluids, as clear capsules, films that are free from particulates, clear cosmetics (lotions and possibly gels in combination with clarified xanthan or borate), etc.

Guar Gum (Galactomannan):

Guar gum is a galactomannan polysaccharide obtained from the seed of the legume Cyanopsis *tetragonolobus*, an annual plant that grows mainly in and and semiarid regions of India and Pakistan. Guar is grown principally as a food crop for animals and as an ingredient in human foods and pharmaceuticals. The guar galactomannan is the major component in the seed endosperm, while the germ portion is mainly protein. In its commercial form, guar gum contains a significant number of impurities, including husks and other cellular debris, with the guar galactomannan comprising only about one-third of the product.

The guar galactomannan is composed of a backbone of $(1\rightarrow4)$-linked $\beta$-D-mannopyranosyl units with single $\alpha$-D-galactopyranosyl units connected by $(1\rightarrow6)$ linkages, with the ratio of galactose to mannose being about 0.55. There are many galactomannans in nature, each varying in this ratio which determines physical and chemical characteristics. Guar galactomannan is soluble in water to form viscous solutions. The actual viscosity values depend upon both the molecular weight and the purity. Guar gum imparts viscosity even in high ionic strength environments. Like konjac and locust bean gum, guar reacts synergistically with xanthan to form very viscous sols and/or gels, depending on proportions and concentrations. It also reacts with alkaline borate to yield amorphous gels.

Guar has numerous applications, some of which have been supplanted by guar derivatives. These range from oil drilling products to textile printing and dyeing to foods, cosmetics and pharmaceuticals.

Locust Bean Gum (Galactomannan):

Locust bean, carob, gum is a galactomannan polysaccharide obtained from the evergreen leguminous tree, *Ceretonia siliqua* L., which grows extensively in Spain is also cultivated in Italy, Cyprus and other Mediterranean countries. Locust bean gum is the refined endosperm of the seed and in its commercial forms locust bean gum contains a significant number of impurities, such as husk residue and cellular debris, depending on the grade.

Locust bean gum, like guar is a galactomannan having the same basic structure. However, there are considerably fewer galactose side-chains in the locust bean galactomannan. The galactose to mannose ratio is 0.25, compared with guar's 0.55. This lower degree of branching is responsible for differences in properties, especially solubility. While guar is mostly soluble in cold water, locust bean gum is not. Dispersions must be heated to about 85° C. to achieve full viscosity. Weak gels are formed when hot sols of locust bean gum are allowed to cool quiescently. Locust bean gum will gel in the presence of borate ion at alkaline pH. It will react synergistically with xanthan to form a gel and will impart elasticity to agar and κ-carrageenan. Locust bean gum is stable over a wide range of pH values, but is rapidly degraded by enzymes found in indigenous microbes.

While guar and guar derivatives have replaced locust bean gum in a number of applications because of cost-effectiveness considerations, locust bean gum is still used in dairy and frozen dessert applications, meat products, pet foods, and the textile industry.

Aloe Acemannan:

Aloe acemannan is a mannan first isolated from *Aloe barbadensis* (var. Miller) by McAnally at Carrington Laboratories and is pharmacologically active. In its commercial state, it contains fine water-insoluble particulates that impart turbidity to the sol. About 80% of the commercial product is a polysaccharide that is composed of a mannose backbone of from 5-50,000 linked units, with >75% being greater than 10,000. Commercial acemannan is partially water soluble and forms viscous sols. It, too, reacts synergistically with xanthan to form elastic gels and alkaline borate to form amorphous gels.

Xanthan Gum:

Xanthan gum is a so-called heteropolysaccharide obtained from the fermentation of *Xanthamonas campestris*. The polymer backbone is composed of (1→4)-linked β-D-glucopyranosyl units, the same as cellulose. Trisaccharide side chains are attached to alternate D-glucosyl units. These are composed of acetyl mannose, glucuronic acid, and mannose residues, with about half of the terminal mannose units containing pyruvate as a 4, 6 cyclic acetal. Many commercial xanthan gum products form somewhat turbid sols, although most of the cellular debris is removed by centrifugation as a processing step. A few higher-value commercial products form an essentially clear sol as a result of an additional filtration step in the processing.

Xanthan gum imparts high viscosity to aqueous solutions at low concentrations. It is compatible with a wide pH range (1-13), being quite stable at ambient temperature for all values. Xanthan gum sols will also add viscosity to solutions having high salt content. Xanthan interacts synergistically with galactomannans, such as guar gum and locust bean gum, and konjac glucomannan to significantly increase viscosity and/or form gels. With these unique properties and its GRAS listing as a food additive, xanthan gum has a wide range of applications, from oil well drilling to salad dressings, cosmetics, and pharmaceuticals.

Clarified Hydrocolloid Composites:

Hydrocolloid composites with varying components in varying weight/weight rations can be prepared by combining their sols and then recovering the product by one of any number of available methods. Although co-processed hydrocolloids and dry physical mixtures of hydrocolloids powders exhibit essentially the same solution properties, dispersion and water absorption properties can be significantly different and vary according to the relative proportions.

Clarified Hydrocolloid/Borate Interaction Products:

At pH values between about 7.5 and 9.0, the borate ion will interact with polymers containing cis-1,2-diols to form more viscous, amorphous systems. These polymeric diols can be synthetic, semi-synthetic, or natural. Some of the more common polymers which undergo this reaction are the polyvinyl alcohols; galactomannans, such as guar gum and locust bean gum; and glucomannans, such as konjac and Aloe (ace) mannans. Depending on the concentration of the polymer, or polymers if two or more are used, the borate, and other additives, if any, the consistency can vary from somewhat viscous fluids to crisp amorphous solids. At selected concentrations of the individual components, the reaction products behave like "healable" solids that will flow at body temperatures. Other soluble and insoluble materials can be added to impart desired properties, such as increased fluid absorption, fluid donation, elasticity, etc.

RELEVANT PRIOR ART

Konjac Clarification:

Snow, W. C. and Renn, D. W. Clarified and cold-melt konjac glucomannan. Patent Nos. WO 09302571 (Feb. 18, 1993) and EP 646133A1 (Apr. 5, 1995).

(Use of considerable heating, a variety of salts and other reagents, along with filter aid to clarify konjac and reduce turbidity (20-100 NTUs), nitrogen and UV spectral absorbance.)

Ohashi, S., Shelso, G. J., Moirano, A. L., and Drinkwater, W. L. Clarified konjac glucomannan. Patent Nos. WO 09303047 (Feb. 18, 1993) and EP 00646134A1 (Apr. 5, 1995).

(Use of considerable heat to dissolve and filter. Impurities precipitated using aluminum sulfate or other salts such as calcium and magnesium sulfate, filtering, then recovering using isopropyl alcohol. Reconstituted konjac has an aqueous sol turbidity potential of less that 20 turbidity units . . . ).

Asahi Kasei Kogyo KK. Glucomannan eye drops. Japan Patent JP6345653 (Dec. 20, 1994).

(Konjac powder, PROPOL PA, was stirred in distilled water for dissolution then centrifuged at 2000 rpm for 10 minutes after which the supernatant had a "first grade white turbidity". This was diluted with distilled water and heated to boiling.)

Maekaji, K. The Mechanism of Gelation of Konjac Mannan. *Agr. Biol. Chem.* 38 (2), 315-321 (1974).

(Insolubles were removed by filtration of a 0.5% sol after stirring the dispersion for two hours at room temperature, by filtration through a glass filter.)

Jacon, S. A., Rao, M. A., Cooley, H. J., and Walter, R. H. The isolation and characterization of a water extract of konjac flour gum. *Carbohydrate Polymers* 20, 35-41 (1993).

(A 0.6% sol of konjac flour in distilled water was agitated for 1.5 hours in a temperature regulated shaker held at approximately 70° C. Insolubles were removed by centrifugation and the supernatants coagulated in 3 volumes of 99% ethanol. Precipitate separated, washed with ethanol, then dried to constant weight at 105° C.)

Morita, S., Morita, H., Shibata, K., and Nakayama, H. Gel for zone electrophoresis. Jpn. Kokai Tokkyo JP 04-248460 [92-248460].

(Clarification of a 0.4% sol by centrifugation, determination of dry weight and using clarified konjac sol directly without drying.)

Nippon Chemifar Co., Ltd. Konjac glucomannan manufacture. Jpn. Kokai Tokkyo Koho JP 58-213001 [83-213001] (Dec. 10, 1983).

(Dissolving overnight at room temperature, centrifuging, coagulating supernatant in ethanol, redissolving, centrifuging, coagulating, and freeze-drying.)

Ogasawara, S. Yamazaki., and Nunomura, W. Electrophoresis on konjac mannan gel. *Seibutsu Butsuri Kagaku* 31(3)155-8(1987).

(50% ethanol for a week, centrifuged, pellets in 80% ethanol for 3 days, centrifuged, washed, filtered. Never dissolved.)

Sugiyama, N. and Shimahara, H. Method of reducing serum cholesterol level with extract of konjac mannan. U.S. Pat. No. 3,856,945 (Dec. 24, 1974).

(Konjac purified by dissolving the konjac flour in water, filtering through 150 mesh nylon then a glass filter, dialyzing and freeze-drying. Product is cloudy when reconstituted. Not a commercially viable process.)

Sugiyama, N. and Shimahara, H. Konjac mannan. U.S. Pat. No. 3,926,322 (Dec. 23, 1975).

(Dissolving in water, removing insolubles by filtration or centrifugation, freeze drying.)

Sugiyama, N. and Shimahara, H. Konjac mannan. U.S. Pat. No. 3,973,008 (Aug. 3, 1976).

(Dissolving in water, removing insolubles by filtration or centrifugation, dialyzing and freeze drying.)

Izumi, T. et al. "Use of glucomannan for the separation of DNA fragments by capillary electrophoresis." *Journal of Chromatography A*, 652, 41-46 (1993).

(Use of non-deacetylated konjac as medium for capillary electrophoresis.)

Ogasawara, S. et al. "Electrophoresis on Konjac mannan gel." Seibutsu Butsuri Kagaku 31, 155-158 (1987).

(Use of konjac gels for electrophoretic separations in non-denaturing buffer systems.)

Morita, S. et al. "Gel media for zone electrophoresis of proteins or nucleic acids." Jpn. Kokai Tokkyo Koho JP 04-248460 (Sep. 3, 1992) CA117: 248159 g (1992).

(Gel matrix of agarose and konjac glucomannan used for nucleic acid and protein separations in non-denaturing buffers.)

Clarified Partially Depolymerized Konjac:

Tomita, M., Ono, J., Fukuwatari, Y., Mizota, T., and Nanba, K. Water-soluble dietary fibers and method for preparation of same. U.S. Pat. No. 4,971,814 (Nov. 20, 1990).

(Konjac powder is partially hydrolyzed using cellulase from *Aspergillus* to yield dietary fibers with average M. W. of 2,000-15,000.)

Tomita, M., Shimamura, S., Fukuwatari, Y. and Nanba, K. Glucomannan hydrolysates for treatment of intestinal cancer. Japan Kokai Tokkyo Koho JP 05-246860 (Sep. 24, 1993). (*Chem. Abstr.*, 120, 14904, 1994).

(Konjac glucomannan was partially hydrolyzed using cellulase and products used as anticholesteremics and antitumor agents in the large intestine.)

Takahashi, R., Ksusakabe, I., Kusama, S., Sakurai, Y., Murakami, K., Maekawa, A., and Suzuki, T. Structures of Glucomanno-oligosaccharides from the Hydrolytic Products of Konjac Glucomannan Produced by a β-Mannanase from *Streptomyces* sp. *Agric. Biol. Chem.*, 48 (12) 2943-2950 (1984).

(Konjac glucomannan hydrolyzed with a purified mannanase.)

Tiefenthaler, K. H. O. and Wyss, U. Water soluble guar product and method for making it. U.S. Pat. No. 4,320,226 (Mar. 16, 1982).

(Depolymerization of guar gum in the presence of alkali).

Guar Gum Clarification:

Naoki, M., Shiyoujo, S., and Taku, T. Purification of galactomannan. Japan Patent JP 63-101402A (Sep. 17, 1984).

(Galactomannan is contacted with an alkali metal hydroxide (e.g., sodium hydroxide) in a medium comprising water or a mixture of water with a hydrophilic organic solvent. The product is then neutralized with neutralizing agent (e.g., hydrochloric or sulfuric acid) to obtain the desired galactomannan.)

Mitsuo, M. Purification of Galactomannan. Japan Patent JP 5-239105 (Sep. 17, 1993).

(An aqueous solution of crude galactomannan is blended with a chelating agent, the blended solution is filtered, and the filtrate is mixed with a precipitating agent for galactomannan to recover and purify galactomannan.)

Mitsuo, M. Purification of Galactomannan. Japan Patent JP 5-239106 (Sep. 17, 1993).

(An aqueous solution of crude galactomannan is blended with a monosaccharide, the blended solution is filtered, and the filtrate is mixed with a precipitating agent for galactomannan to recover and purify galactomannan.)

Hirofumi, N., Hideki, Y., and Michiyoshi, A. Purification of galactomannan. Japan Patent JP 63-035606 (Feb. 16, 1988).

(The pH of an aqueous solution obtained by dissolving a galactomannan-containing product such as crushed guar beans, locust beans or tara beans in hot water at 70° C. or above is adjusted to 4.5-6.5 by adding an acid to the solution. A filter aid (e.g., Perlite) of a mean particle diameter of 15-20 microns is added to this aqueous solution. This solution is filtered to remove insoluble matter such as protein and cellulose, and a hydrophilic organic solvent such as methanol or isopropyl alcohol is added to the filtrate to precipitate gum. This gum is dehydrated by pressing, dried and ground.)

Noble, O., Turquois, T, and Taravel, F. R. Rheological Properties of Galactomannan-Based Gels. Part I—Guar and Hydroxypropylguar Gels in Alkaline Media. *Carbohydrate Polymers* 12, 203-217 (1990).

(Guar gum purified by dispersing in stirring water at 60° C. and stirring rapidly for 1 or 2 hours. Insoluble material was removed by centrifugation and supernatants precipitated by addition of 95% isopropyl alcohol. Precipitate washed with ethanol and vacuum dried.)

Locust Bean Gum Clarification:

Braun et al. Preparation of Vegetable Gum Solutions. U.S. Pat. No. 2,144,522 (Jan. 17, 1939).

(Decolorizing and clarifying locust bean gum by adding activated carbon and aluminum sulfate, filtering, and coagulating in isopropyl alcohol.)

Foster. Treatment of Manno Galactan Gums. U.S. Pat. No. 3,346,556. (Oct. 10, 1967)

(Example 5 discloses a means for clarifying locust bean gum by adding diatomaceous earth and filtering.)

Naoki, M., Shiyoujo, S., and Taku, T. Purification of galactomannan. Japan Pat. No. JP 63-101402A (Sep. 17, 1984).

(Galactomannan is contacted with an alkali metal hydroxide (e.g., sodium hydroxide) in a medium comprising water or a mixture of water with a hydrophilic organic solvent. The product is then neutralized with neutralizing agent (e.g., hydrochloric or sulfuric acid) to obtain the desired galactomannan.)

Mitsuo, M. Purification of Galactomannan. Japan Patent JP 5-239105 (Sep. 17, 1993).

(An aqueous solution of crude galactomannan is blended with a chelating agent, the blended solution is filtered, the filtrate is mixed with a precipitating agent for galactomannan to recover and purify galactomannan.)

Mitsuo, M. Purification of Galactomannan. Japan Patent JP 5-239106 (Sep. 17, 1993).

(An aqueous solution of crude galactomannan is blended with a monosaccharide, the blended solution is filtered, the filtrate is mixed with a precipitating agent for galactomannan to recover and purify galactomannan.)

Hirofumi, N., Hideki, Y., and Michiyoshi, A. Purification of galactomannan. Japan Patent JP 63-035606 (Feb. 16, 1988).

(The pH of an aqueous solution obtained by dissolving a galactomannan-containing product such as crushed guar beans, locust beans or tara beans in hot water at 70° C. or above is adjusted to 4.5-6.5 by adding an acid to the solution.

A filter aid (e.g., pearlite) of a mean particle diameter of 15-20 microns is added to this aqueous solution. This solution is filtered to remove insoluble matter such as protein and cellulose, and a hydrophilic organic solvent such as methanol or isopropyl alcohol is added to the filtrate to precipitate gum. This gum is dehydrated by pressing, dried and ground.)

Morikawa, M. and Suzuki, S. Purification of locust bean gum. JP 63-105004 (May 10, 1988).

(Crude locust bean gum is dissolved in warm water and filtering, followed by recovering the locust bean gum and drying.)

Xanthan Gum Clarification:

Kang, K. S. and Petitt, D. J. "Xanthan, Gellan, Welan, and Rhamsan" in Industrial Gums, Polysaccharides and Their Derivatives. Third Edition. Whistler, R. L. and BeMiller, J. N., Editors. Academic Press, 1992, page 346.

("A clear product can be produced by diluting the fermentation liquor and clarifying it by filtration.")

Rinaudo, M., Milas, M., and Kohler, N. Enzymatic clarification process for improving the injectivity and filtrability of xanthan gums.

(Abstract: Enzymatic treatment, in aqueous dispersion, of a xanthan gum containing bacteria cell residues and microgels, as impurities, by means of a Basidomycete cellulase . . . , improved the infectivity and filtrability thereof.)

Murofushi, K., Nagura, S., Homma, T., and Armentrout, R. Process for preparation of a purified xanthan gum. European Patent Application No. 92311401.1 (Jun. 30, 1993).

(Heat treatment followed by alkaline protease and lysozyme, then recovering the xanthan from the broth. "A clear aqueous solution of the xanthan gum may be obtained without complex procedures.")

Aloe Acemannan Clarification:

McAnnalley, B. H. Process for preparation of aloe products, products produced thereby and compositions thereof. U.S. Pat. No. 4,735,935 (Apr. 5, 1988).

(Patent covering isolation of acemannan.)

McAnnalley, B. H. Process for preparation of aloe products, products produced thereby and compositions thereof. U.S. Pat. No. 4,917,890 (Apr. 5, 1988).

(Patent covering isolation of acemannan.)

Vilkas, E. and Radjabi-Nassab, F. The glucomannan system from Aloe vahombe (liliaceae), III. Comparative studies on the glucomannan components isolated from the leaves. Biochemie 6, 1123-1127 (1986).

(Aqueous sol prepared and centrifuged. Supernatant coagulated in ethanol.)

Mandal, G. and Das, A. Structure of the glucomannan isolated from the leaves of Aloe barbadensis (MILLER) *Carbohydrate Research* 87, 249-256 (1980).

(Aqueous sol prepared and centrifuged.)

Hydrocolloid Co-processing:

Yoshida, H., Kamiya, S., Takano, Y., and Toba, S. Instant konjac mannan food. Jpn. Kokai Tokkyo Koho JP 62-96061 (May 2, 1987). Chem. Abstracts 107, 133074 (1987).

("A solution containing konjac mannan and xanthan gum (95-5:5-95) at acidic to neutral pH is dried to give an instant konjac mannan food with high water absorbency and reconstitution rate"—konjac was not deacetylated.)

Kira, M. Preparation of agar gel (tokoroten) containing glucomannan. JPN. Kokai Tokkyo Koho JP 05-199853 (Aug. 10, 1993). (CA 119:224827 1993).

("Tokoroten with improved strength and elasticity and yet without the odor of agar is prepared by the addition of glucomannan and thickening agents into the weak alkali-treated agar. After the mixture is heated to dissolve, it can be deodorized and decolorized prior to gelling.")

Tako, M. Synergistic Interaction between Xanthan and Konjac Glucomannan in Aqueous Media. *Biosci. Biotech. Biochem.* 56(8), 1188-1192 (1992).

(Synergistic gel formation described for native, de-pyruvated, and de-acetylated clarified xanthan and clarified konjac. For clarification of the xanthan, a 0.1% sol of commercial xanthan in distilled water was heated at 90° C. for 30 minutes, then cooled to room temperature and filtered through Celite 545. The filtrate was made to 0.1% with KCl, coagulated in 2 volumes of ethanol, the precipitate collected and dried in vacuo. The konjac flour was soaked in 50% ethanol for three days at room temperature. The suspension was filtered and the residue was dissolved by stirring with distilled water at 90° C. for 30 minutes. The sol was filtered through Celite 545 and the clear filtrate coagulated in 2 volumes of ethanol. The precipitate was collected and dried in vacuo.)

Nippon Chemipharm. Manufacture of konnyaku glucomannan for electric migration gel materials. Jpn. Kokai Tokkyo Koho JP 58-213001 (Dec. 10, 1983).

(Purification by forming a sol, centrifuging, and coagulating the supernatants in ethanol.)

Kawano, N. Instantly Soluble Glucomannan Composition, Its Use and Preparation. Japan Patent Disclosure No. H5-38263. (Feb. 19, 1993).

(Fluidized bed granulation and drying of mixed polysaccharides, including konjac.)

Fujihara, K. and Nakagawa, T. Method of producing readily soluble poly-saccharides. Japan Patent Disclosure No. 1982-[Showa 57]-028102 (Feb. 15, 1982).

(Dissolving polysaccharides or mixtures and spray-drying. Only mixture given is locust bean gum/xanthan.)

Musson, G. D. and Prest, C. T. Thermo-irreversible edible gels of glucomannan and xanthan gums. U.S. Pat. No. 4,894,250 (Jan. 16, 1990).

(Preparation of deacetylated konjac gels containing xanthan and, optionally, carrageenan, pectin, algin, agar, gellan, and/or guar.)

Fukuda, T. Manufacture of dried konjac with mono- and/or oligosaccharides. Japan Kokai Tokkyo Koho JP 04-08257 (Jan. 13, 1992) CA 116:172746c (1992).

(Dry konjac is manufactured by mixing konjac with mono- and/or oligosaccharides and drying. Rehydration in water restores its original gel state.)

Kawano, K. Instantly soluble glucomannan composition, its use and preparation. Japanese Unexamined Patent Application Disclosure H5-38263 (Feb. 19, 1993) WPI Acc No: 93-096400/12.

(Non-deacetylated konjac is co-processed with a variety of hydrocolloids (carrageenan, xanthan, agar, alginates, pectin, starch CMC, polyacrylates, etc.) by mixing in the fluid state, then drying to give products that are readily dispersible and soluble in water.)

Renn, D. W., Lauterbaugh, G. E., and Hemmingsen, P. Soluble dried *cassia* alloy gum composition and process for making same. U.S. Pat. No. 4,952,686 (Aug. 28, 1990).

(The initial patent on the technique of co-processing insoluble or poorly soluble hydrocolloids with one or more other hydrocolloids to impart solubility or other important properties. Clarified *Cassia* galactomannan coprecipitated with various gums to improve solubility of the galactomannan. Composite of clarified *Cassia* gum and xanthan is highly water absorbent.)

Snow, W. C. and Renn, D. W. Glucomannan spongeous matrices. Patent Nos. WO 09402029A1 (Feb. 3, 1994) and EP 650348A1 (May 5, 1995).

(Konjac co-processed with agar or at least one other gelling polysaccharide to form a spongeous matrix.)

Yoshida, H. et al. Instant Konjak mannan food. Jpn. Kokai Tokkyo Koho JP 62-96061 (May 2, 1987) CA 107: 133085f (1987).

(Solution of konjac mannan and xanthan at acidic to neutral pH was dried to give an instant konjac mannan product with high water-absorbency and reconstitution rate—konjac was not deacetylated.)

Applegren, C. H. Process for preparing a product comprising guar-gum. U.S. Pat. No. 4,754,027 (Jun. 28, 1988).

(Guar composites produced by granulating non-clarified guar with sols of non-gelling hydrocolloids.)

Toba, S., Yoshida, H., and Tokita, T. Konjac mannan-containing reversible gel. U.S. Pat. No. 4,676,976. (Jun. 30, 1987).

(Reversible konjac/xanthan gel formation with strongest gels at 4:1 ratio.)

Ishikawa, H. et al. Preparation of freeze-resistant konjac. Japanese Patent Application No. 60-4019, Filed Jan. 16, 1985, Abstract published Dec. 12 1986.

(Co-processed, but not dried, deacetylated konjac and insoluble alginate.)

Ueno, K. Preparation of konjak resistant to freezing. Jpn. Kokai Tokkyo Koho JP 05-00055 (Jan. 8, 1993) CA118: 146606d (1993).

("Konjak resistant to freezing is prepared by adding starch and natural gums, e.g., locust bean gum and tara gum.")

Umehara, S. et al. A dry gel containing starch and konnyaku mannan as an instant konnyaku. Jpn. Kokai Tokkyo Koho JP 62-259550 (Nov. 11, 1987) CA108: 149158p (1988).

(Dried gel of deacetylated konjac and starch that hydrates to gel particles in boiling water.)

Vernon, A. J. et al. Thermo-irreversible gelling system and edible materials based thereon. European Patent Application Publication No.: 0 050 006 (Jul. 10, 1981).

(Konjac and carrageenan gelled using phosphate buffer and heat.)

Suto, S. et al. Scanning electron microscopy of blend of konjac mannan and hydroxypropyl cellulose. *Sen-I Gakkaishi* 48(8) 437-440 (1992).

(Gel prepared from blend of konjac and hydroxypropyl cellulose.)

Ikeda, M. and Harada, S. "Low calorie processed food made with gel particles of glucomannan coagulum." U.S. Pat. No. 5,213,834 (May 25, 1993).

(Encapsulated organic acids to neutralize alkaline gels of konjac and konjac gels made with the addition of other hydrocolloids, such as carrageenan, alginates, locust bean gum, agar, xanthan, etc.)

Kawano, N. Instantly soluble glucomannan composition, its use and preparation. Japanese Unexamined Patent Application Disclosure H5-38263 (Feb. 19, 1993) WPI Acc No: 93-096400/12.

(Non-deacetylated konjac is coprocessed with a variety of hydrocolloids (carrageenan, xanthan, agar, alginates, pectin, starch CMC, polyacrylates, etc.) by mixing in the fluid state, then drying to give products that are readily dispersible and soluble in water.)

Hydrocolloid Films, Foams, Gels, and Sponges:

D. A. Harper, J. H. Morgan, S. Nochumson, M. V. Ostrovsky, D. W. Renn, W. C. Snow. "Agarose compositions for nucleic acid sequencing." U.S. Pat. No. 5,455,344 (Oct. 3, 1995).

(Sequencing nucleic acids using a polysaccharide gel medium in the presence of denaturing agents—includes deacetylated konjac gels.)

Snow, W. C. and Renn, D. W. Glucomannan spongeous matrices. Patent Nos. WO 09402029A1 (Feb. 3, 1994) and EP 650348A1 (May 3, 1995).

(Konjac co-processed with agar or at least one other gelling polysaccharide to form a spongeous matrix upon freezing and thawing.)

Masao, K. Glucomannan/polyhydric alcohol composition and film prepared therefrom. European Patent Application Publication No. 0 273 069 (Jun. 7, 1988).

(Konjac glucomannan films and applications.)

Kakizaki, T. and Kdubodera, M. Edible glucomannan film for food packing. Jpn. Kokai Tokkyo Koho JP 62-126950 (Jun. 9, 1987). (CA107, 613, (1987).

("A composition containing glucomannan, optionally other natural polysaccharides, and one or more of polyhydric alcohols, sugar alcohols, monosaccharides, disaccharides, and oligosaccharides is kneaded, dissolved in water, and made into a film to produce an edible film for food packaging.")

Merritt II, F. M. Edible film and method. U.S. Pat. No. 5,962,053. (Oct. 5, 1999).

(Abstract: Described is an edible, water insoluble film which is a blend of polysaccharide and protein and, in particular, a ternary blend of konjac flour as a major constituent, agar and gelatin. Also described is a method of forming the film including a deacetylating step to insolubilze the konjac flour.)

Nussinovitch, A. Sponge comprising expansion product of hydrocolloid. WO 9417137 A (Aug. 4, 1994).

("Sponge is formed by foaming one or more hydrocolloids selected from agar, carrageenan, gelatin, alginate, starch, pectin, gellan konjak, mannan or xanthan locust bean gum. The sponge containing a plasticiser (esp. glycerol, sorbitol or other polyol, a sugar or sugar substitute, bubbles of a gas other than air and opt. a flavoring agent or taste enhancer.")

Tanabe, O. et al. Fiber-rich foods made from Konjak flour. Jpn. Kokai Tokkyo Koho JP 01-256366 (Apr. 4, 1988) CA113: 57776p (1990).

(Water-insoluble, gelled deacetylated konjac recovered by freeze thawing—not dried.)

Sakamoto, J and Tanuma, H. Low-calorie food products containing konjac mannan and processes for preparing the same. U.S. Pat. No. 5,116,631.

(Non-deacetylated konjac as a foam stabilizer for egg white meringues.)

Ford, D. M. and Cheney, P. A. "Air or oil emulsion food product having glucomannan as sole stabilizer-thickener." U.S. Pat. No. 4,582,714.

(Non-deacetylated konjac as a aerated food stabilizer.)

Nozaki, H. et al. Devil's tongue-containing whip cream. Japanese Patent Application No. 01-177050, Filed Jul. 11, 1989, Abstract published May 7, 1991.

(Prepared alkaline deacetylated gel added to cream while whipping.)

Sawaguchi, K. Meringue. Japanese Patent Application No. 57-126718, Filed Jul. 22, 1982, Abstract published May 12, 1984.

(Use of non-deacetylated konjac to stabilize meringues.)

Sugino, Y. Porous gel foods and their manufacture from glucomannan and whipped egg white. Jpn. Kokai Tokkyo Koho JP 04-11853 (Jan. 16, 1992).

(Egg white/konjac whipped together then set (deacetylated) with calcium hydroxide and heat.)

Bakis, G. et al. "Production of polysaccharide foam comprises mechanically foaming aqueous solutions of soluble polysaccharide, e.g., alginate, hyaluronate, carrageenan, chitosan or starch." WO 9400512 (Jan. 6, 1994) WPI Acc No: 94-026166/03.

(Mechanically foaming an aqueous solution of a polysaccharide and used as wound dressing etc.)

Borate Interaction Products:

Renn, D. W. Solid borate-diol interaction products for use in wounds. World Patent WO 09953968A1 (Oct. 28, 1999).

(Interaction of sodium tetraborate with PVA and polysaccharides, glucomanans and galactomannans, having a cis 1,2-diol configuration in their structure.)

Hogi, T. and Kameda, N. Transparent konnyaku mannan gels for optical products. JP 05-194603 (93-194603) Aug. 3, 1993.

(Konjac mannan and sodium tetraborate product for contact lenses and medical optical devices.)

Muller, E. G. Borated polysaccharide absorbents and absorbent products. U.S. Pat. No. 4,624,868. Nov. 25, 1986.

(Guar gum as an exemplification of cis-1,2-diol polysaccharides is first hydrated then thickened by cross-linking with borax and finally dried to a powder to flake form, preferably by freeze drying. The resulting particles can absorb up to 100 times their weight or more of aqueous fluids such as urine. Absorbent articles, such as disposable diapers, bandages, and the like are formed with the borax-cross-linked guar gum as absorbent.)

Anderson, R. L. Flushable premoistened wiper. U.S. Pat. No. 4,362,781. Dec. 7, 1982.

Premoistened wiper comprising a nonwoven web impregnated with a modified guar gum (phosphated) (5-14% of fiber weight) and wet with an aqueous lotion containing borate ions. Lotion also contains an organic hydroxy or keto acid or salt thereof (such as potassium citrate) capable of complexing with borate ions.

Zimmerman, V. et al. Thin sanitary products with a prefabricated absorbent body. International Application Publication No. WO 95/17147. Jun. 29, 1995.

(Fibers coated with particles of a galactomannan, or derivative thereof.)

Rademacher, K. and Fritsce, U. (Sebapharma) Dressing system. WO 9203172. Feb. 20, 1992.

(The bandage, dressing or support matrix consists of a biocompatible, open-pored plastic foam with a hydrogel embedded in the pores. The hydrogel is formed from a borate-modified Guar gum . . . ).

SUMMARY OF INVENTION

The invention is directed to a process of producing a clarified hydrocolloid which, when hydrated, forms a clear sol, the said process comprising: (a) soaking a hydrocolloid-containing material dispersed in water until the hydrocolloid is hydrated; (b) stirring the hydrated hydrocolloid until a homogenous particulate-containing sol is obtained; (c) removing the insoluble particulates to produce a clarified sol; (d) removing any remaining particulates in the clarified sol by filtration; and (e) recovering clarified hydrocolloid directly from the filtrate.

The insoluble particulates in step (c) can be removed by centrifugation or by coarse filtration.

The hydrocolloid can be selected from the group consisting of konjac glucomannan, guar gum, locust bean gum, aloe mannan, agar, agarose, algins, β-, κ-, λ- ι-carrageenans, chitosan, collagen, curdlan and other β-1,3-glucans, fig seed gum (galacturonan), gellan, hyaluronic acid, pectins, *Rhizobium* gum, Porphyridium cruentum polysaccharide, starches (amylose, amylopectin), acacia gum, gum arabic, chondroitin sulfates, dextrans, flaxseed gum, gum ghatti, inulin (fructan), karaya gum, larch arabinogalactan, levan (fructosan), *cassia* gum, tara gum, fenugreek gum, oat glucans, okra mucilage, psyllium seed gum, pullulan, quince seed gum, rhamsan, scleroglucan, succinoglucan, tamarind gum, gum tragacanth, wellan, and xanthan gum.

In cases where the hydrocolloid is insoluble at ambient temperature, the hydrated colloid can be heated to solubilize the hydrocolloid before proceeding with step (c).

When the hydrocolloid is konjac glucomannan, the hydrated konjac can be heated to a temperature of less than or equal to about 45° C.

In conducting step (b) the hydrated colloid can be shear-stirred until a homogenous sol is obtained. Furthermore, in conducting step (e), water-miscible alcohol can be added to the solution.

The hydrocolloid recovered from the filtrate in step (d) can be dried to form a solid. The hydrocolloid after drying can be ground to a consistency of about 100 mesh.

The viscosity of the clarified hydrocolloid sol obtained after the performance of step (e) can be within about 70 to 90 percent of the viscosity of the untreated hydrocolloid sol at equivalent hydrocolloid concentration.

The sol of one or more other hydrocolloids can be added before recovery to yield clarified hydrocolloid composites.

A second clear hydrocolloid sol can be added before step (e) is performed. Alternatively, a second unclarified hydrocolloid sol can be added before step (c). Furthermore, a dry first hydrocolloid and a second dry hydrocolloid can be mixed before performing step (a).

The invention is also directed to a process of producing a hydrocolloid which when hydrated forms a clear sol comprising soaking the hydrocolloid in water until the hydrocolloid is hydrated, shear-stirring the hydrated hydrocolloid until the homogenous particulate-containing sol is obtained, centrifuging the sol to remove any filter-blinding material, adding a filter aid to the centrifugate, filtering the centrifugate at a temperature less than about 45° C., recycling the filtrate until it is clear, recovering the clarified hydrocolloid by miscible alcohol coagulation, and maintaining re-solubility characteristics of the clarified hydrocolloid by washing with high titer alcohol.

The invention includes a process of producing a konjac glucomannan which, when hydrated, forms a clear konjac glucomannan sol which comprises dispersing a konjac containing flour in water, permitting the dispersed konjac-water mixture to stand at room temperature until the konjac is hydrated, subjecting the hydrated konjac mixture to a high shear stirring action to produce a smooth sol, centrifuging the smooth sol to remove insoluble particulates in the mixture, adding a filter aid to the filtrate and mixing the filter aid into the mixture, filtering the mixture at a temperature less than 45° C. to obtain a clear filtrate, treating the clear filtrate with isopropyl alcohol to coagulate the konjac glucomannan, collecting the konjac coagulated konjac, and drying the konjac.

The invention also incorporates a process of producing a guar gum devoid of additive salts and degrading effects of acids which when hydrated forms a clear guar gum sol, which comprises dispersing a guar gum containing material in water by first wetting the material with isopropyl alcohol and then adding water to the mixture, heating the mixture with stirring until homogenous and hydration of the guar is complete, centrifuging the mixture, adding a filter aid to the mixture and mixing the filter aid thoroughly into the mixture, filtering the mixture, adding an isopropyl alcohol to the filtrate obtained from the filtration step, collecting coagulated guar gum, drying the guar gum and grinding the collected coagulated guar gum into a powder.

The invention is also directed to a process of producing a locust bean gum powder devoid of additive salts and acids which when hydrated forms a clear locust bean gum sol comprising adding a locust bean gum containing material to water, heating the locust bean gum-water mixture to the boiling point, stirring the mixture until a homogenous mixture is obtained, centrifuging the mixture, adding a filter aid to the centrifugate, mixing the mixture until homogeneous, filtering the mixture to obtain a clear filtrate, adding isopropyl alcohol to the filtrate to coagulate the locust bean gum, collecting the coagulated locust bean gum, drying the coagulated locust bean gum and grinding to yield a powder.

The invention includes in a further embodiment a process of producing an aloe mannan which when hydrated forms a clear aloe sol comprising adding an aloe mannan containing material to water, permitting the aloe-water mixture to stand until the aloe mannan is hydrated, raising the temperature of the aloe-water mixture to the boiling point, mixing the mixture until a homogenous mixture is obtained, centrifuging the mixture to remove undesirable particulates, adding a filter aid to the centrifugate, filtering the mixture, coagulating the aloe mannan by adding a miscible alcohol to the mixture, collecting the coagulated aloe mannan, drying the coagulated aloe mannan and grinding it to obtain a powder.

The invention is also directed to a process of producing a xanthan gum which when hydrated forms a clear xanthan gum sol comprising dispersing a xanthan gum containing material in water, heating the xanthan-water mixture to the boiling point, mixing the mixture until homogeneity is obtained, centrifuging the mixture to remove undesirable particulates, adding a filter aid to the mixture, heating to boiling, filtering the mixture, coagulating the xanthan by adding a miscible alcohol to the filtrate, collecting the coagulated xanthan gum and drying the coagulated xanthan gum and grinding it to obtain a powder.

The invention in a further version includes a process of producing a hydrocolloid composite which when hydrated forms a clear hydrocolloid composite sol comprising dispersing a first clarified hydrocolloid and at least a second clarified hydrocolloid in water, adding sodium chloride to the sol, mixing the mixture to obtain a homogenous mixture, and coagulating the first hydrocolloid with the second hydrocolloid as a precipitate by adding a miscible alcohol, collecting the coagulated hydrocolloid composite, drying the composite and grinding it to form a powder.

The invention is also directed to a clarified hydrocolloid or a composition comprising clarified konjac and clarified guar gum which composition forms a clear sol when mixed with water, a composition comprising clarified konjac and clarified xanthan gum which composition forms a clear sol when mixed with water, a composition comprising clarified xanthan gum and clarified guar gum which composition forms a clear sol when mixed with water, a composition comprising clarified aloe mannan and clarified guar gum which composition forms a clear sol when mixed with water, a composition comprising clarified konjac and clarified agar which composition forms a clear sol when mixed with water, a composition comprising clarified aloe mannan and clarified konjac which composition forms a clear sol when mixed with water, a composition comprising clarified konjac and clarified carboxymethyl cellulose which composition forms a clear sol when mixed with water, or a composition comprising clarified guar gum and clarified carboxymethyl cellulose which composition forms a clear sol when mixed with water.

The invention is also directed to a process of forming low sol viscosity hydrocolloids by having the particulate hydrocolloids absorb hydrogen peroxide and then heating the hydrocolloids or permitting the hydrated colloids to remain at room temperature for an extended period.

The invention includes a process of producing a reduced viscosity konjac which comprises adding hydrogen peroxide to the konjac-containing solid, blending the mixture until a homogenous paste is obtained, heating the paste to about 65° C. for about five hours, cooling the mixture to about room temperature, adding a filter aid to the mixture, filtering the mixture to obtain a clear filtrate, adding isopropyl alcohol to the clear filtrate to precipitate konjac, and collecting the coagulated konjac, drying the coagulated konjac and grinding it to form a powder.

DRAWINGS

In drawings which illustrate specific embodiments of the invention, but which should not be construed as restricting the spirit or scope of the invention in any way.

DETAILED DESCRIPTION OF INVENTION

Figure 1:
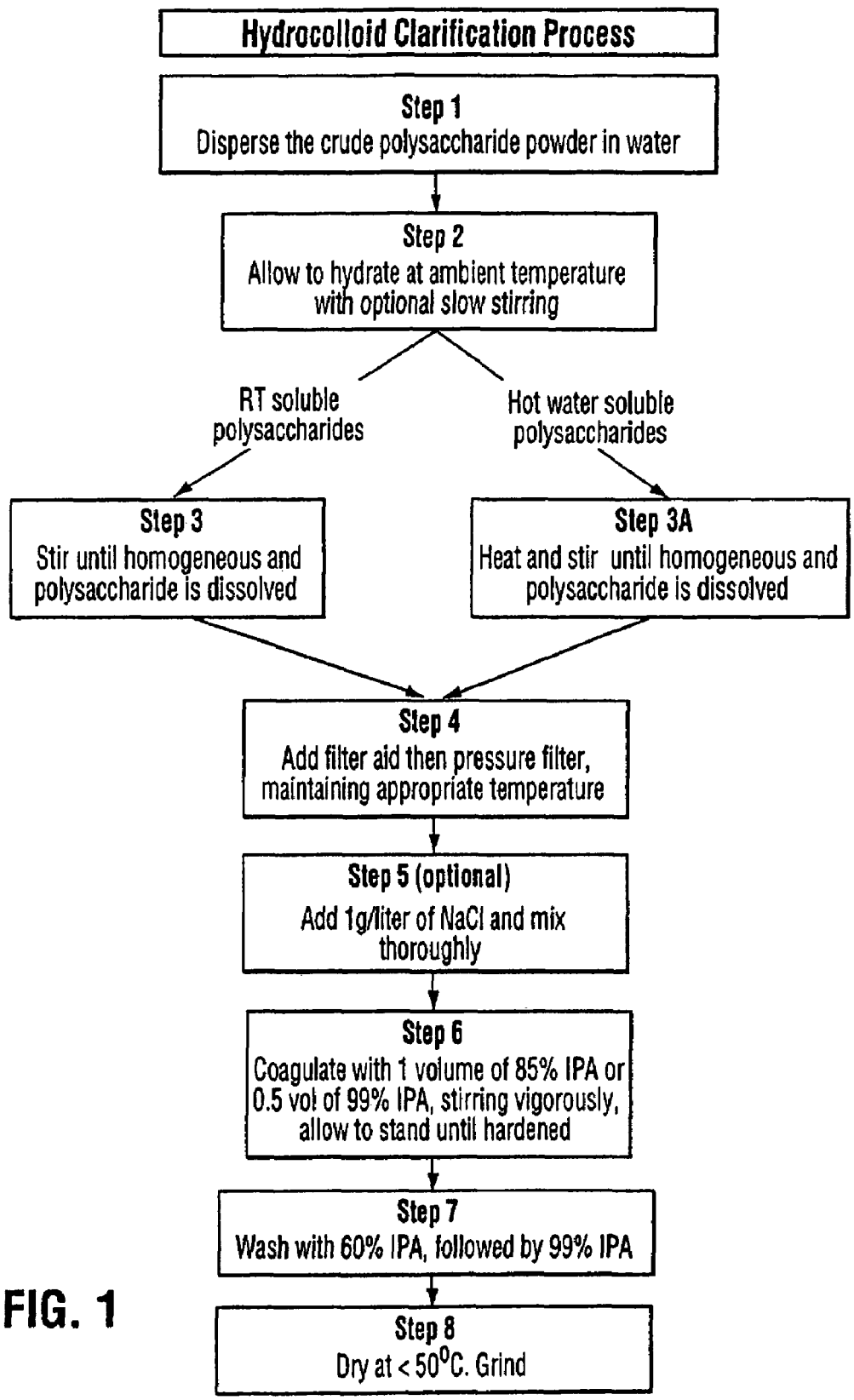
FIG. 1 illustrates a schematic flow sheet of the hydrocolloid clarification process according to the invention.
Figure 2:
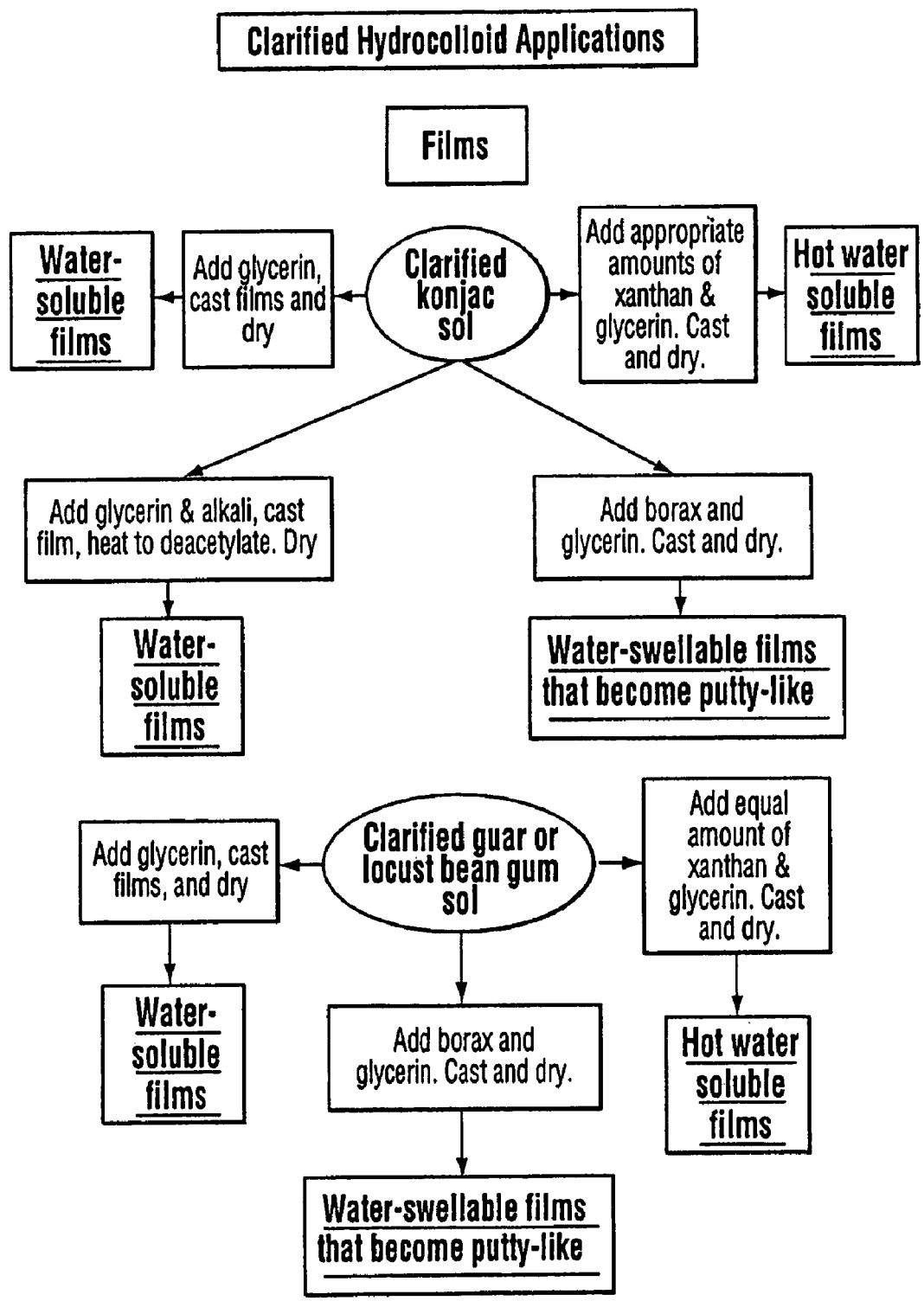
FIG. 2 illustrates a schematic diagram of the practical applications that can be made of the clarified hydrocolloids according to the invention.

Although there are a number of published procedures in patent and journal literature for clarifying hydrocolloids, such as glucomannans, galactomannans, and fermentation polysaccharides, particularly for structure determination and derivatization, no clarified products having significant sales seem to be available commercially. This fact tends to demonstrate that none of these methods are cost-effective or, in some cases, capable of scale-up, or in other cases, the clarified hydrocolloids suffer a loss in properties, when compared to the unclarified hydrocolloids. In the case of locust bean gum and konjac, clarified products are manufactured by, for example, FMC Corporation to be sold as blends. Significant viscosity reduction is evident with their commercial products, but not evident in products produced by this invention.

We have developed a simple but non-obvious process that results in dry hydrocolloid products that, when reconstituted, form clear viscous sols, free from essentially all particulates and retain desirable physical properties, unlike commercial products. The method according to the invention appears to surmount the difficulties with prior processes by minimizing heating and high-shear stirring in the dissolution step. This keeps the impurities in as large a particulate state as possible. The process follows with centrifuging to remove the filter-blinding materials, filtering the mixture at a temperature less than about 45° C., except when the polysaccharides are insoluble at this temperature, using an appropriate filter aid, recycling the filtrate until it is crystal clear, recovering the clarified hydrocolloid through isopropyl alcohol coagulation, and maintaining ready re-solubility in the clarified products with a final wash of high-titer alcohol. This procedure can be used to clarify virtually all hydrocolloids, including konjac, guar gum, locust bean gum, Aloe acemannan, and xanthan gum, to name a few.

The clarified hydrocolloids obtained by the method according to the invention can be recovered directly, such as by coagulation in isopropyl alcohol, or can be combined with one or more other hydrocolloid sols and then recovered. The process of the invention can impart unique properties to the composite clarified hydrocolloids that are different from the original clarified hydrocolloids. Such properties cannot be achieved by direct blends of the solid materials. In one embodiment of the invention, a simple yet unique way for preparing low-viscosity, clarified depolymerized konjac has also been discovered and developed.

The products and process of the invention differ from the prior art in a number of respects. There are in existence a number of patents and publications that disclose procedures for "clarifying" konjac and other hydrocolloids. The products derived from most of these procedures are either unsatisfactory or the method is laborious and not cost-effective. Using the method according to the invention for clarifying polysaccharides, it is likely that cost-effective products can be obtained. These clarified polysaccharides can either be blended with other ingredients, co-precipitated with other hydrocolloids, or co-dried with other materials, leading to a number of interesting and useful, commercially feasible, clarified polysaccharide-based products.

The key inventive and successful factors with this process, and what makes it unique and different from existing konjac clarification processes, and other hydrocolloid clarification procedures is a combination of the way the crude hydrocolloids are reconstituted to minimize the possibility for degradation or conversion to insoluble entities, maintaining the impurities in as large a particle size as possible, the centrifugation method used to remove the filter-blinding solids, the filtration, and the polysaccharide recovery. All these steps lead to retention or enhancement of viscosity and other desirable properties.

In particular, according to the present invention, the methods for producing clarified guar and bean gum do not require the addition of salts or acids, for example, alkaline earth metal salts, to accomplish clarification. The inventors have observed that the addition of alkaline earth metal salts to the galactomannans is not advantageous because they produce degrading effects and remove a number of soluble components, some of which are beneficial and contribute synergistically to the stabilization and preservation of the galactomannans. It is known, for example, that both guar and locust bean gum, in the crude state, are prone to depolymerization, and excessive removal of native material and soluble components can cause destabilization of the clarified products. The inventive methods for producing clarified guar gum and locust bean gum powder avoid this problem by not requiring the use of alkaline earth metal salts.

The use of hydrogen peroxide in a heterogeneous reaction, i.e., imbibing the peroxide into the dry konjac powder and allowing the reaction to take place until the mixture becomes fluid, also is unique.

Clarifying Other Natural Polysaccharides

In addition to the polysaccharides mentioned in this discussion, there is no reason to believe that the following natural polysaccharides cannot be clarified using appropriate temperature and time modifications of the basic method. A non-limiting list follows.

Gelling

Agar, agarose, algins, β-, κ-, ι-carrageenans, chitosan, collagen, curdlan and other β-1,3-glucans, fig seed gum (galacturonan), gellan, hyaluronic acid, pectins, *Rhizobium* gum and *Porphyridium cruentum* polysaccharide.

Non-Gelling

Acacia gum, gum arabic, α-carrageenan, chondroitin sulfates, dextrans, flaxseed gum, gum ghatti, inulin (fructan), karaya gum, larch arabinogalactan, levan (fructosan), *cassia*, tara, fenugreek and other galactomannans, oat glucans, okra mucilage, psyllium seed gum, pullulan, quince seed gum, rhamsan, scleroglucan, starches (amylose, amylopectin), succinoglucan, tamarind gum, gum tragacanth, wellan, and xanthan gum.

EXAMPLES

Although isopropyl alcohol (2-propanol) coagulation has been used as the recovery method in many of the examples given, it is conceivable that other methods, such as spray drying, freeze drying, etc., can be used as well, to recover the clarified polysaccharides and composites.

Clarification Procedures

Clarified Konjac (High Viscosity)

Example 1

(Using NaCl (aq.) to dissolve the Konjac, Direct Filtration) (MBI Notebook DWR1, p. 38):

Using a 2-litre Pyrex measuring bowl, 10 grams of AMOPHOL LG konjac powder (Shimizu Chemical Corp., lot LHB27) was dispersed in 1 litre of de-ionized water (tap water may be satisfactory) containing 25 grams of dissolved NaCl using a hand-held Braun blender/homogenizer to assure complete dispersion and minimize clumping. The container was covered with plastic film and the contents heated to boiling in a microwave oven. Occasional hand-stirring with a spatula was needed initially to keep the swelling particles from settling. The hot mixture, containing both dissolved konjac and swollen particles as well as particulate impurities, was allowed to cool to near room temperature. A brief high shear blending with the Braun Blender was used to assist in the dissolution of the swollen particles. Fifty grams of Dicalite SpeedPlus filter aid was added, along with 500 ml of de-ionized water. The mixture was blended briefly (Braun Blender), then filtered through a cloth pad in a 2-litre pressure filtration device, recycling until crystal clear. The clear filtrate was collected (~1400 ml) and then coagulated in 3 litres of 85% isopropyl alcohol (IPA) (aq.). After ½ hour, the white, voluminous fibrous coag was collected on fine-mesh Nitex cloth, squeezed, pulled apart, washed in 500 ml 60% IPA for ½ hour using magnetic stirring, again collected on Nitex, squeezed, pulled apart, and washed, with magnetic stirring in 500 ml of 99% IPA. The washed, clarified konjac fibers were again collected on Nitex cloth, squeezed, then pulled apart and dried in a forced air oven at about 40° C. The dried, fluffy white product, 7.4 g or 74% yield, without moisture correction, was ground to −20 mesh. A clear 0.5% sol was formed when this material was dissolved in 0.5% NaCl(aq.) A 1% sol in de-ionized water exhibited a viscosity of 10,870 mPas at 25° C., using the #2 spindle and 0.3 rpm settings on the Brookfield DV-II+Viscometer. An equivalent concentration of the starting material (1.35% based on 74% yield) had a viscosity of 5,250 mPas at 22° C., #2 spindle, 0.3 rpm.

Example 2

(MBI Notebook DWR1, pp. 16, 26, 29, 32, 36, 37):

In a similar manner other konjac flour-based products from Shimizu Chemical Industries, AMOPHOL TS, PROPOL RS, and PROPOL RX—H were clarified. Yields obtained were 72.0%, 65.5%, and 58.2% respectively.

Example 3

(No Salt, no Centrifugation) (MBI Notebook DWR1, p. 46):

Five grams of AMOPHOL TS (Lot TGJ22, Shimizu Chemical Corporation) was dispersed in 0.5 litres of de-ionized water using a spatula. The mixture was heated to boiling in a microwave oven. An additional 250 ml of de-ionized water was added and stirred in using an Arrow overhead stirrer. To this was added 25 grams of Dicalite Speed Plus filter aid and stirred until homogeneous. This was filtered at room temperature through a thick cloth pad in a 2-litre pressure filtration apparatus (PFA). Only 200 ml of clear filtrate was collected before a tough film blinded the filter. The filtrate was coagulated in 400 ml of 85% IPA, stirring with a spatula while pouring. After one-half hour, the coag was collected on Nitex cloth, squeezed, and washed by stirring with 200 ml of 60% IPA for 20 minutes, again collecting on Nitex cloth and squeezing. 200 ml of 99% IPA was used for the final wash. After collecting and squeezing, the coag was dried at about 38° C. in a one-pass hot air oven. After grinding to −20 mesh, 0.4 g (about 60% yield) of white powder was obtained.

In a like manner, 10 g of Konjac Flour M (Shimizu Chemical Corporation, Lot 981027) was clarified with 6.37 g (63.7% yield) being obtained. The viscosity of a 1% sol of the clarified material was 1,156 mPas compared with a 1% viscosity of 656 mPas for the Konjac Flour.

Example 4

(Water, Centrifugation, Filtration) (MBI Notebook DWR3, p. 10)

Filtration difficulties were encountered with direct filtration of the konjac sol because of the formation of a waxy flexible film on the surface of the filter aid. The procedure was modified to include a centrifugation step before filtration. Filtration of the combined centrifugates was rapid and able to be done at low pressure input.

To 1 litre of de-ionized water was added 6.7 g of Konjac Flour AP (Shimizu Chemical Corporation, Lot 990820) and dispersed using a wire whisk attachment on a Braun hand-held blender. After standing at room temperature for about one hour to hydrate, the high-shear blade attachment to the Braun blender was used to prepare a smooth sol. This sol was distributed into 4 screw-cap polypropy-lene centrifuge bottles and centrifuged at 11,000 rpm for 40 minutes, using a Sorvall RC2-B centrifuge. After the supernatants were removed by decantation and combined, 50 g of Dicalite Speed Plus filter aid was added and mixed in thoroughly. This was filtered through a felt pad in a 2-litre pressure filtration device. Filtration was rapid and accomplished at <20 psi. The filtrate (800 ml) was sparkling clear. To this was added 500 ml of 99% IPA and the stirred with a spatula to mix thoroughly. A mucoid coag formed which on standing became firm enough to handle. This was collected on Nitex cloth, squeezed, pulled apart and washed in 300 ml of 99% IPA and again collected on Nitex cloth, squeezed and dried at about 38° C. in a one-pass hot air oven. After grinding to −20 mesh, 2.38 g (about 35.5% yield) of white powder was obtained. A 1% sol in de-ionized water was clear and exhibited a viscosity of 8,125 mPas at 21.3° C., using the #2 spindle and 0.3 rpm settings on the Brookfield DV-II+Viscometer. Conductivity was 20 µS at 21.5° C. using an Oakton TDSTestr™ conductivity meter.

Two pilot plant scale-ups of this procedure yielded white powders having viscosities of 25,250 and 29,030 mPas respectively for 1% sols compared with 32,500 for a 1.35% sol of the Konjac Flour AP.

Clarified Partially De-Polymerized Konjac (Low Viscosity)

Example 5

(MBI Notebook 3, pp. 2, 4.)

To 350 g of AMOPHOL TS (Shimizu Chemical Corporation, Lot THF 19) in a stainless steel 5-quart Kitchen Aid mixing bowl was added 1400 ml of 10% hydrogen peroxide and the mixture blended until it became a stiff homogeneous paste. The bowl was covered with Saran Wrap and placed in a 65° C. water bath for 5 hours, occasionally mixing with a spatula. During this time a nearly clear, slightly yellow, low-viscosity fluid was obtained. After allowing the reaction product to cool to room temperature, 25 g of Dicalite Speed Plus filter aid was added and mixed in with a broad spatula. This mixture was filtered through a 30 g pre-coat of the filter aid on a felt pad in a 2-litre pressure filtration device. The clear filtrate (ca. 1500 ml) was coagulated in 4.5 litres of rapidly stirring 99% IPA. The fine precipitate was collected on Nitex cloth, squeezed, washed for 20 minutes in 4 litres of stirred 99% IPA, collected on Nitex cloth, squeezed, and dried at about 38° C. in a one-pass hot air oven. 299.5 g (86.5%) of fine white granular powder was obtained. A clear 10% solution (w/w) of this material in de-ionized water was easily prepared. Properties of this 10% solution were as follows: viscosity=1.4 mPas, pH=2.98, turbidity=16.4 N.T.U.

Clarified Guar Gum

Example 6

(MBI Notebook DWR3, p. 33)

Commercial grade guar gum, PROCOL F (Lot: A7265B), was obtained from Polypro International, Minneapolis, Minn. To 10 g was added 30 ml of 99% IPA and the mixture stirred with a spatula until homogeneous. While agitating with the wire whisk attachment to a Braun hand-held blender, one litre of de-ionized water was added rapidly and stirred until nearly homogeneous. After standing at room temperature for one hour to complete hydration, the mixture was heated to boiling using a microwave oven then homogenized using the blender attachment. The mixture was reheated to boiling and transferred to 2-250 ml polypropylene screw-cap centrifuge bottles and centrifuged for 30 minutes at 11,000 rpm, using a Sorvall RC2-B centrifuge. After the supernatants were removed by decantation and combined, 25 g of Dicalite Speed Plus filter aid was added and mixed in thoroughly. This was filtered through a 30 gram pre-coat of the Speed Plus on a felt pad in a 2-litre pressure filtration device. The filtrate (ca. 800 ml) was sparkling clear. This was coagulated in 800 ml of rapidly stirring 99% IPA. The coag was collected on Nitex cloth, squeezed, pulled apart and washed in 250 ml of 99% IPA and again collected on Nitex cloth, squeezed and dried at about 38° C. in a one-pass hot air oven. After grinding to −20 mesh, 4.65 g (46.5% yield) of white powder was obtained. The 1% sol viscosity of clarified guar was >2,000 mPas compared with 2,575 mPas for a 1% sol of the PROCOL F.

Clarified Locust Bean Gum

Example 7

(MBI Notebook DWR1, p. 43)

Using a Braun hand-held mixer, 2 g of commercial locust bean gum (T.I.C. Gums, Por/A, FCC Powder, Lot: P00124) was suspended in 300 ml of de-ionized water containing 2 g of NaCl. This was covered with Saran Wrap and heated to boiling in a microwave oven. The mixture was re-blended, 10 g of Dicalite SpeedPlus filter aid was added and mixed in thoroughly. This was then filtered through a 10 g pre-coat of the filter aid on a felt pad in a 500 ml pressure filtration vessel, recycling until sparkling clear. The clarified locust bean gum was recovered by coagulating the filtrate (ca. 250 ml) in 500 ml of 85% IPA. The coag was collected on Nitex cloth, squeezed, and washed successively with 200 ml 60% IPA, and 200 ml of 99% IPA, each time stirring for ½ hour, then collecting the coag on Nitex cloth and squeezing. Drying was effected at about 38° C. in a one-pass hot air oven. After grinding to –20 mesh, 1.28 g (64% yield) of white powder was obtained. A 1% sol of the clarified locust bean gum was clear and colorless and exhibited a viscosity of 438 mPas compared with a 1% sol viscosity of 212 mPas for the starting material.

Clarified Aloe Acemannan

Example 8

(MBI Notebook DWR3, p. 26):

To 5 g of Aloe glucomannan (Carrington Laboratories' acemannan 95008, Lot: 10608) was added sufficient 99% IPA to just wet the powder evenly when stirred with a spatula. Using the wire whisk attachment to the Braun hand-held mixer, 750 ml of de-ionized water was added. The dispersed suspension was allowed to stand until fully hydrated. The mixture was brought to a boil in a microwave oven and blended using the blender attachment to the Braun. This sol was distributed into 3-250 ml screw-cap polypropylene centrifuge bottles and centrifuged at 10,000 rpm for 30 minutes, using a Sorvall RC2-B centrifuge. After the supernatants were removed by decantation and combined, 25 g of Dicalite Speed Plus filter aid was added and mixed in thoroughly. This was filtered through a 30 g pre coat of the filter aid on a felt pad in a 2-litre pressure filtration device. The filtrate (650 ml) was clear but not sparkling. The clarified Aloe glucomannan was recovered by adding 650 ml of 99% IPA and mixing thoroughly. After standing at room temperature for an hour to harden, the coag was collected on Nitex cloth, squeezed, and washed using 300 ml 99% IPA stirring for ½ hour, then collecting the coag on Nitex cloth and squeezing. Drying was effected at about 38° C. in a one-pass hot air oven. After grinding to –20 mesh, 2.0 g (40% yield) of white powder was obtained. A 1% sol of the clarified Aloe glucomannan was clear and very viscous.

Clarified Xanthan Gum

Example 9

(MBI Notebook DWR2, p. 7)

Ten grams of Keltrol T (Monsanto, Lot 8K0725K) was dispersed in one litre of deionized water using a Braun hand-held blender. Dissolution was completed by heating to boiling in a microwave oven. Twenty grams of Celite (3 micron) was added and dispersed uniformly. The mixture was brought to boiling and filtered through a 30 gram pre-coat in a pressure filtration device. About 920 ml of filtrate was collected. This was coagulated in 2 litres of 99% IPA after mixing in 20 ml of 10% NaCl. The coagulum was collected on Nitex cloth, squeezed, and placed in 500 ml of 85% IPA overnight. The coag was collected and dried at about 38° C. in a single-pass, forced air oven. The white product was ground to –20 mesh yielding 6.8 g (68%) of powder. The viscosity of a 1% sol was 3,000 mPas compared with a viscosity of 3,562 mPas for a 1% sol of the starting material.

Co-Precipitation (Hydrocolloid Composites)

The following examples are only a small part of the infinite number of combinations possible. Concentrations can be altered as can the materials for co-processing. Additionally, other soluble and/or insoluble materials can be included.

Clarified Konjac/Carboxymethyl Cellulose (CMC)
(3:1)

Example 10

(MBI Notebook DWR2, p. 63)

One litre of 1% clarified konjac (Marine BioProducts, Lot 268) sol, 335 ml of 1% CMC (Hercules, Cellulose gum Type 7MF PH, Lot 66989) sol, and 14 ml of 10% NaCl (aq.) solution were combined, mixed thoroughly with a Braun hand-held blender, then coagulated in 2.5 litres of rapidly stirred 99% IPA. The white stringy coag was collected on a fine sieve, squeezed to remove fluid, pulled apart, then washed by stirring with one litre of 99% IPA for 15 minutes. The washed coag was collected on Nitex cloth, squeezed, then dried in a forced-air oven at about 38° C. After grinding to –20 mesh, 10.7 g (80.1% yield) of white product was obtained. This was more readily soluble in water than was the clarified konjac control and rapidly formed a clear sol, almost spontaneously.

Clarified Konjac/Hydroxyethyl Cellulose (HEC)
(4:1)

Example 11

(MBI Notebook DWR1, p. 59):

One percent sols of clarified konjac (Marine BioProducts, Lot 257) and HEC (Hercules, Natrosol, 250L NF, FP10, Lot 13879) were prepared. To 400 ml of the konjac sol was added 100 ml of the HEC sol, the two mixed together thoroughly using a Braun hand-held blender, heated to boiling, then coagulated in 1 litre of 85% IPA while stirring with a spatula. The coag was collected on a Nitex cloth, squeezed, then washed successively with 500 ml of 85% IPA for 20 minutes and 250 ml of 99% IPA for 10 minutes, each time stirring, then collecting on Nitex and squeezing to remove as much fluid as possible. Drying was done in a forced-air oven at about 38° C. After grinding to –20 mesh, 3.2 g (64% yield) of white product was obtained. This was more readily soluble in water than was the clarified konjac control and rapidly formed a clear sol.

Clarified Konjac/Hydroxypropylmethyl Cellulose (HPMC) (4:1)

Example 12

(MBI Notebook DWR1, p. 59):

One percent sols of clarified konjac (Marine BioProducts, Lot 257) and HPMC (Hercules, Benecel, MP-824, FP10, Lot 13510) were prepared. To 240 ml of the konjac sol was added 60 ml of the HPMC sol, the two mixed together thoroughly using a Braun hand-held blender, heated to boiling, then coagulated in 500 ml of 85% IPA while stirring with a spatula. The coag was collected on a Nitex cloth, squeezed, then washed successively with 300 ml of 85% IPA for 20 minutes and 300 ml of 99% IPA for 10 minutes, each time stirring, then collecting on Nitex and squeezing to remove as much fluid as possible. Drying was done in a forced-air oven at about 38° C. After grinding to −20 mesh, 1.3 g (43.3% yield) of white product was obtained. (The low yield is due to the fact that HPMC is somewhat soluble in the alcohol concentrations used.) The konjac/HPMC composite was more readily soluble in water than was the clarified konjac control and rapidly formed a clear sol.

Clarified Konjac/Clarified Locust Bean Gum (1:1)

Example 13

(MBI Notebook DWR2, p. 50)

Twenty millilitres each of 1% clarified konjac sol (Marine BioProducts, Lot 268) and 1% clarified locust bean gum (Marine BioProducts, DWR3-43B) were prepared using de-ionized water. These were combined, mixed thoroughly, heated to boiling in a microwave oven, and coagulated in 100 ml of 85% IPA. The coag was collected on Nitex cloth, squeezed, pulled apart, and washed by stirring for ten minutes with 100 ml of 85% IPA. After collecting on Nitex cloth, squeezing, and pulling apart, the washed coag was dried in a one-pass hot air oven at about 38° C., then ground to −20 mesh (0.31 g, 77% yield).

Clarified Konjac/Clarified Guar (3:1)

Example 14

(MBI Notebook DWR3, p. 19)

To 100 ml of clarified guar (Marine BioProducts, DWR2-21-1) sol was added 300 ml of a 1% aqueous sol of clarified konjac TS (Marine BioProducts, Lot 268), the sols mixed well with a spatula and then coagulated in 800 ml of 99% IPA while stirring with a spatula. The fibrous white coag was collected on Nitex cloth and squeezed to remove adhering fluid. After washing in 500 ml of 99% IPA for 0.5 hours, the coag was collected, squeezed, then dried in a one-pass hot air oven at about 38° C. The coag was ground to −20 mesh, giving 3.55 g (88.8% yield) of white powder. When placed in water it hydrated rapidly and dissolved.

Clarified Konjac/Agar (1:1)

Example 15

(MBI Notebook DWR2, p. 78)

One litre aqueous sols each of clarified konjac (Marine BioProducts, Lot 268) and agar (Marine BioProducts, Lot 276) were prepared. Both were heated to near boiling using a microwave oven, mixed thoroughly along with 30 ml of 10% NaCl (aq.). The composite was recovered by pouring into 5 litres of rapidly stirring 85% IPA. The white, fibrous coag was shredded using a Braun hand-held blender, then collected on Nitex cloth and squeezed to remove the adhering fluid. The coag was washed successively using 2 litres of 85% IPA then 1.5 litres of 99% IPA, each time stirring 20 minutes, collecting on Nitex and squeezing. Drying was done at about 38° C. in a one-pass forced air oven. After grinding to −20 mesh, 30.0 g (75% recovery) of white powder was obtained. A 1% gel prepared from this powder was elastic, nearly clear and colorless.

Clarified Konjac/Xanthan (1:1)

Example 16

(MBI Notebook DWR2, p. 78)

One and a half litres each of 1% aqueous sols of clarified konjac (Marine BioProducts, Lot 268) and xanthan (Monsanto Keltrol T, Lot 8K0725K) were prepared. These sols were combined, along with 30 ml of 10% NaCl, mixed thoroughly using a Braun hand-held blender, then coagulated by pouring into 6 litres of rapidly stirring 85% IPA. The fibrous white coag was collected on a fine sieve, squeezed, and pulled apart. After washing by stirring for 20 minutes in 1 liter 85% IPA, the coag was again collected, squeezed to remove the adhering alcohol, pulled apart and dried on Nitex cloth in a one-pass 38° C. forced air oven. After grinding to −20 mesh, 28.3 g (94% yield) of off-white powder was obtained. This powder rapidly absorbed about 200× its weight of de-ionized water or about 50× its weight of 1% NaCl to form a particulate gel. When heated and cooled, a clear elastic gel was formed. Aqueous gels of 0.06% were prepared that had a Jello®-like consistency.

Clarified Guar/Xanthan (1:1)

Example 17

(MBI Notebook DWR4, p. 7)

To a dry mixture of 2.5 g of clarified guar (MBI Lot DWR3-44-1) and 2.5 g of Keltrol T xanthan (Monsanto lot 8K0725K) was added about 10 ml of 99% isopropyl alcohol and the mixture was stirred to ensure complete wetting. While being stirred with an overhead stirrer, 500 ml of deionized water was added. After dispersion was complete, the mixture was heated to boiling in a microwave oven and 400 ml was coagulated in 1 litres of 99% IPA using a spatula to agitate the mixture. After standing for one hour at ambient temperature to harden the precipitate, the product was collected using a plastic sieve. After squeezing, the precipitate was transferred to 300 ml of 99% IPA and stirred for about 20 minutes. The precipitate was collected on a Nitex cloth, squeezed, and dried in a 38° C. single-pass, forced-air oven. After grinding to −20 mesh, 3.16 g of powder was obtained. When 50 ml of water was added to 250 mg of this sample, the water was rapidly absorbed to form a relatively clear, semi-coherent gel. When this was brought to boiling in a microwave oven, it dissolved rapidly to form a clear, viscous solution, which when cooled, formed a clear, elastic gel.

Clarified Hydrocolloid Konjac Gels, Films, Foams and Sponges

When konjac glucomannan is heated with alkali, about pH=~7.5-11, deacetylation occurs and the resulting gel product is water insoluble and thermostable. If the gel formed by deacetylation is frozen and thawed, a tough, coherent spongeous mass is formed. Deacetylated konjac gels, films, foams, sponges, beads, and other forms can be prepared. Porosity of the sponges depends on the rate of freezing of the sols.

The deacetylated konjac films are boiling water insoluble and are formed from a clarified konjac sol by adding alkali before casting the film, then heating to ensure that deacetylation occurs. Films can be prepared from a konjac/xanthan sol that are clear and hot water (>85° C.) soluble. If films are prepared from a clarified konjac sol, without heating, they are cold water soluble.

Clarified Konjac Gels

Example 18

(MBI Notebook DWR3 p. 65)

To 250 ml of a 1% clarified konjac sol (MBI Lot 268) was added 2.5 ml of 1 NaOH. This was blended quickly, yet thoroughly, using the wire whisk attachment of the Braun hand-held blender. This mixture was rapidly poured equally into three 100 ml beakers. These were covered with plastic wrap and placed in a 99° C. oven to deacetylate and form a gel. This gel was not completely clear like the starting konjac sol, but slightly hazy. Gels containing 0.5% and 0.25% clarified konjac were also prepared in this manner.

Clarified Konjac Films

Water Soluble Films

Example 19

(MBI Notebook DWR3, p. 64)

To 300 ml of a 1% clarified konjac sol (MBI Lot 268) in deionized water was added 1.5 g of glycerol. After mixing well, the sol was brought to boiling in a microwave oven, let stand in a 99° C. oven for 15 minutes to deaerate and poured into three oblong plastic dishes (11 cm×18.5 cm). The sols were dried to films at about 38° C. in a one-pass forced air oven. These films were tough, flexible, and fully transparent. When wet with water, the film rapidly absorbed water and disintegrated, then gradually dissolved.

Hot Water Soluble Films

Example 20

(MBI Notebook DWR3, p. 64)

To 300 ml of a hot (<80° C.) aqueous 0.5% sol of 1:1 clarified konjac/xanthan (see Example 16) was added 1.5 g of glycerol and the mixture stirred thoroughly. After reheating to boiling, the sol was placed in a 99° C. oven for 15 minutes to deaerate, then poured into three oblong plastic dishes (11 cm×18.5 cm). The sols were dried to films at about 38° C. in a one-pass forced air oven. These films were tough, flexible, and fully transparent. When wet with water, the film rapidly absorbed water and became quite tough and elastic, while remaining transparent.

Water Insoluble Films

Example 21

(MBI Notebook DWR3, p. 64)

To 100 ml of a 1% clarified konjac sol (MBI Lot 268) in deionized water was added 0.5 g of glycerol, and 1.0 ml of 1 M NaOH. After mixing thoroughly with the wire whisk attachment of the Braun hand-held mixer, the mix was poured into an oblong plastic dish (11 cm×18.5 cm). The dish was covered and placed in a 99° C. oven to set. The cover was removed and the dish placed in a 38° C., one-pass, forced air oven to dry. The resulting film was not completely transparent, but slightly hazy. It was tough and flexible and rapidly imbibed water, maintaining its toughness and flexibility.

Clarified Konjac Foams

Water Insoluble Deacetylated

Example 22

(MBI Notebook DWR3 p. 63)

In the stainless steel bowl of a Kitchen Aid mixer was placed 300 g of 1% clarified TS konjac (MBI, Lot 268), 40 g of a 3% aqueous sol of hydroxyethyl cellulose (Hercules Natrosol 250 m Pharm, Lot FP 10 13809) as a foaming agent, and 4 g of glycerol as a plasticizer. This was mixed using the standard paddle attachment. This was insufficient HEC to induce foaming so about 5 ml of a solution of hand-soap (unknown origin) shavings was added and after beating for about 10 minutes on high speed, a thick white foam resulted. Three ml of 1M NaOH was added and rapidly beat into the foam. The foam was portioned into a variety of covered plastic dishes, covered and placed into a 99° C. oven for about one hour to deacetylate and form a thermo-irreversible gel matrix. The syneresate was removed by decantation and three of the foams dried in a 38° C. one-pass forced-air oven. When a sample of the white foam was placed in deionized water, it hydrated rapidly.

Water Insoluble Deacetylated, Frozen and Thawed

Example 23

(MBI Notebook DWR3, p. 63)

The remaining three foams from Example 22 were placed, covered tightly, in a −18° C. freezer overnight. The frozen foams were thawed in hot running water and the water expressed from the jelly fish-like, tough foamy masses using a thumb and forefinger. The resulting partially de-watered foams were covered with 99% IPA and let stand for about 1 hour. The fluid was expressed by squeezing and the procedure repeated. These were then blotted between paper towels and dried on a rack in the hood. The resulting white parchment-like sheets rapidly hydrated to form tough jelly fish-like masses.

Clarified Konjac/Xanthan Foams

Example 24

(MBI Notebook DWR3, p. 72)

Three hundred millilitres of a hot sol containing 3.0 g of 1:1 clarified konjac/xanthan and 1 g of glycerol was prepared in a 2-litre measuring bowl. This was placed in a boiling water bath and 2 ml of a solution of hand-soap shavings in deionized water was added. The mixture was then foamed using the wire whisk attachment on a Braun hand-held mixer. The foam was distributed into plastic dishes at room temperature. Setting was rapid. The foams were removed from the dishes and placed on a rack in a 38° C. one-pass forced air oven to dry. Rehydration in water was rapid and a voluminous, low strength, clearish foamy mass resulted. In 1% NaCl, rehydration was slower and resulted in a significantly lower volume, stronger, elastic hydrated foam.

Clarified Konjac Sponges

Example 25

(MBI Notebook DWR3, p. 65)

The gels from Example 18 were placed in a −18° C. freezer overnight to freeze. They were then thawed using warm running tap water. The 1% gel/sponge had very small pores and was too firm to squeeze to fully convert to a sponge. The lower percentage gels, when frozen and thawed, gave jellyfish-like sponges. When soaked in 99% IPA, squeezed and dried, parchment like disks were obtained that imbibed water, but more slowly and to a lesser extent than the frozen, thawed, and dried foams.

Clarified Hydrocolloid/Borate Interaction Products

Preparation of these amorphous solids consists of forming a sol of the cis-1,2-diol, and thermostable additives, if any, by dispersing the components in cool water, heating the mixture to boiling, adding hot aqueous sodium tetraborate, and allowing to cool. Other components can be added at suitable temperatures. If film preparation is desired, the hot sol can be distributed on a surface to form a film and the film used as is or dried. For powders or granules, the solid diol can be triturated with a concentrated solution of sodium tetraborate with or without glycerol. For in situ-formed coatings, the sponge, cloth, gauze, or other material to be coated can either be dipped into the hot mix, removed and drained, and optionally dried. Alternatively, the coatings can be applied by successively dipping the material to be coated into the borate solution, draining, blotting, blowing, or squeezing to remove the excess, if desired; dipping next into a cis-1,2-diol polymer solution, with or without additives; and finally again into the borate solution. If desired, this series can be repeated.

Possible additives to the polymeric cis-1,2-diol reaction mixture used for any of the products are: other borate-reactive and/or non-reactive hydrocolloids; reactive or non-reactive low molecular weight substances; insoluble particulates, both swellable and non-swellable, including charcoal and encapsulated chemical and/or biological reagents, ion-exchange resins, etc.; therapeutics; enzymes; antibodies; antimicrobials; etc.

Gelling hydrocolloids, such as agar, gellan, carrageenan, and curdlan can be added to the clarified konjac, guar, locust bean gum, or aloe mannan sols before cross-linking with borate. At concentrations where the hydrocolloid would have formed a firm gel alone, combinations can yield products with unique properties.

The following two examples are not meant to be limiting, since many different combinations of cis-1,2-diol containing molecules will cross-link using borates and can be combined with each other and/or non-reactive molecules to give unique properties. In addition, glycerol and/or other compatible plasticizers can be added and clear, hydratable films prepared.

Clarified Konjac/Borate Interaction Products

"Gels"

Example 26

(MBI Notebook DWR3, p. 73)

To three 50-ml samples of 1% clarified konjac (MBI, lot 268) in deionized water was added selected amounts of a 3.79% borax solution (=2.0% $NaB_4O_7$). After mixing thoroughly with a spatula, they were covered with plastic wrap and heated to boiling in a microwave oven, stirred again, and allowed to cool to room temperature. The following observations were made:

| ml borax | Observations (all clear and colorless) |
| --- | --- |
| 1 | mucoid consistency and slimy feel (free konjac) |
| 5 | flexible and slightly moist |
| 15 | firmer and slightly fragile |

Films

Example 27

(MBI Notebook DWR3, p. 73)

Films were prepared from the gels in Example 26 by adding a small amount of glycerol, heating to boiling in a microwave oven, mixing thoroughly and pouring into 11 cm×18.5 cm Rubbermaid plastic dishes. The gels were dried to films using a 38° C. one-pass, forced-air oven. Clear flexible films resulted that rapidly hydrated in deionized water.

Foam

Example 28

(MBI Notebook DWR3, p. 73)

To 50 ml of the 1% clarified konjac sol (see Example 26) was added 1 ml of a hand-soap shavings sol and the mixture whipped to a stiff foam using the wire whisk attachment of the Braun hand-held blender. Two millilitres of the 3.79% borax solution was added and whipped in. A very elastic foam resulted. This was placed on inverted plastic dishes and dried using a 38° C. one-pass, forced-air oven. A thin whitish dried foam resulted that hydrated rapidly in deionized water to a tough, elastic thin foam.

Clarified Guar/Borate Interaction Products

"Gels"

Example 29

(MBI Notebook DWR3, p. 73)

To three 50-ml samples of 1% clarified guar (MBI, lot DWR3-33-1) in deionized water was added selected amounts of a 3.79% borax solution (=2.0% $NaB_4O_7$). After mixing thoroughly with a spatula, they were covered with plastic wrap and heated to boiling in a microwave oven, stirred again, and allowed to cool to room temperature. The following observations were made:

| ml borax | Observations (all clear and colorless) |
| --- | --- |
| 1 | flexible and slightly fragile |
| 5 | flexible and fragile |
| 15 | firmer and fragile |

Films

Example 30

(MBI Notebook DWR3, p. 73)

Films were prepared from the gels in Example 29 by adding a small amount of glycerol, heating to boiling in a microwave oven, mixing thoroughly and pouring into 11 cm×18.5 cm Rubbermaid plastic dishes. The gels were dried to films using a 38° C. one-pass, forced-air oven. A clear flexible film resulted from the first gel that was lowest in borate. The other two formed more brittle films. All hydrated rapidly in deionized water, became putty-like, and gradually dissolved when excess water was present.

Foam

Example 31

(MBI Notebook DWR3, p. 73)

To 50 ml of the 1% clarified guar sol (see Example 29) was added 1 ml of a hand-soap shavings sol and the mixture whipped to a stiff foam using the wire whisk attachment of the Braun hand-held blender. One millilitre of the 3.79% borax solution was added and whipped in. A very elastic foam resulted. This was placed on inverted plastic dishes and dried using a 38° C. one-pass, forced-air oven. Thin, whitish dried foams resulted that hydrated rapidly in deionized water to a tough, elastic thin foam that, over a period of time, continued swelling.

Clarified Guar/Xanthan Film

Example 32

(MBI Notebook DWR4, p. 7)

A clear, hot water soluble film was prepared using the 1:1 guar/xanthan composite sol described in Example 17. After adding 0.5 g of glycerin and 100 ml of deionized water, the remaining sol (100 ml) was heated to boiling in a microwave oven and distributed equally into each of two oblong Rubbermaid™ plastic storage dishes and dried in a single pass, forced-air oven. The clear, flexible films rapidly absorbed ambient temperature water and became weak and swollen. In hot water, they dissolved.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A process of producing a clarified guar gum powder which when hydrated forms a clear guar sol that is free of particulates, comprising the steps of:

dispersing a guar gum containing material in water by wetting the material with isopropyl alcohol, and then adding water to form a mixture;

heating the mixture with stirring to boiling until homogenous and hydration of the guar gum is complete;

centrifuging the mixture;

adding a filter aid to the mixture and mixing the filter aid thoroughly into the mixture;

filtering the mixture to produce a filtrate;

adding isopropyl alcohol to the filtrate obtained from the filtration step to coagulate guar gum;

collecting the coagulated guar gum;

drying the guar gum; and grinding the dried guar gum into a powder, wherein salts or acids are not added to said mixture or said filtrate during any of said steps, thereby producing a clarified guar gum powder devoid of additive salts and degrading effects of acids.

2. A process of producing a clarified guar gum powder which when hydrated forms a clear guar sol that is free of particulates, comprising the steps of:

dispersing a guar gum containing material in water by wetting the material with isopropyl alcohol, and then adding water to form a mixture;

heating the mixture with stirring to boiling until homogenous and hydration of the guar gum is complete;

centrifuging the mixture;

adding a filter aid to the mixture and mixing the filter aid thoroughly into the mixture;

filtering the mixture to produce a filtrate;

adding isopropyl alcohol to the filtrate obtained from the filtration step to coagulate guar gum;

collecting the coagulated guar gum;

drying the guar gum; and grinding the dried guar gum into a powder, wherein an alkaline earth metal salt is not added to said mixture or said filtrate during any of said steps.

* * * * *